US008747858B2

(12) United States Patent
McNeely et al.

(10) Patent No.: US 8,747,858 B2
(45) Date of Patent: Jun. 10, 2014

(54) STAPHYLOCOCCUS AUREUS SURFACE PROTEIN SA1789 AND PROTECTIVE VACCINE BASED THEREON

(75) Inventors: Tessie B. McNeely, Gwynedd Valley, PA (US); Hongxia Fan, North Wales, PA (US); Mark Andrew Miller, Wyndmoor, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/809,736

(22) PCT Filed: Jul. 8, 2011

(86) PCT No.: PCT/US2011/043274
§ 371 (c)(1),
(2), (4) Date: Jan. 31, 2013

(87) PCT Pub. No.: WO2012/021229
PCT Pub. Date: Feb. 16, 2012

(65) Prior Publication Data
US 2013/0122034 A1    May 16, 2013

Related U.S. Application Data

(60) Provisional application No. 61/363,893, filed on Jul. 13, 2010, provisional application No. 61/366,360, filed on Jul. 21, 2010.

(51) Int. Cl.
*C07K 14/195* (2006.01)
(52) U.S. Cl.
USPC ........................................ 424/190.1; 530/350
(58) Field of Classification Search
None
See application file for complete search history.

(56) References Cited

U.S. PATENT DOCUMENTS

| 6,593,114 B1 | 7/2003 | Kunsch et al. |
| 2006/0115490 A1 | 6/2006 | Masignani et al. |
| 2006/0177462 A1 | 8/2006 | Anderson et al. |
| 2009/0317421 A1 | 12/2009 | Missiakas et al. |
| 2011/0229508 A1 | 9/2011 | McNeely et al. |
| 2011/0229509 A1 | 9/2011 | McNeely et al. |

FOREIGN PATENT DOCUMENTS

| WO | WO 01/98499 A1 | 12/2001 |
| WO | WO 02/059148 A2 | 8/2002 |
| WO | WO 2005/009378 A2 | 2/2005 |
| WO | WO 2005/009379 A2 | 2/2005 |
| WO | WO 2005/079315 A2 | 9/2005 |
| WO | WO 2005/086663 A2 | 9/2005 |
| WO | WO 2005/115113 A2 | 12/2005 |
| WO | WO 2006/033918 A2 | 3/2006 |
| WO | WO 2006/078680 A2 | 7/2006 |

OTHER PUBLICATIONS

Greenspan et al. (Nature Biotechnology 7: 936-937, 1999).*
Bowie et al (Science, 1990, 257:1306-1310).*
Baba et al., "Genome and virulence determinants of high virulence community-acquired MRSA", 2000, Lancet 359:1819-1827.
Brady et al., "Identification of *Staphylococcus aureus* Proteins Recognized by the Antibody-Mediated Immune Response to a Biofilm Infection" 2006, Infect. Immun., 74:3415-26.
Clarke et al., "Identification of in Vivo—Expressed Antigens of *Staphylococcus aureus* and Their Use in Vaccinations for Protection against Nasal Carriage" 2006, J. Infect. Dis. 193:1098-108.
Cook et al., "*Staphylococcus aureus* capsule type 8 antibodies provide inconsistent efficacy in murine models of staphylococcal infection" Human Vaccines 5:254 (2009).
Etz et al., "Identification of in vivo expressed vaccine candidate antigens from *Staphylococcus aureus*" 2002, Proc. Natl. Acad. Sci. USA 99:6573-6578.
Gatlin et al., "Proteomic profiling of cell envelope-associated proteins from *Staphylococcus aureus*" 2006, Proteomics 6:1530-49.
Josefsson et al., "Protection against Experimental *Staphylococcus aureus* Arthritis by Vaccination with Clumping Factor A, a Novel Virulence Determinant" 2001, J. Infect. Dis. 184:1572-1580.
Joyce et al., "Isolation, structural characterization, and immunological evaluation of a high-molecular-weight exopolysaccharide from *Staphylococcus aureus*" 2003, Carbohydrate Research 338:903-922.
Kuklin et al., "A Novel *Staphylococcus aureus* Vaccine: Iron Surface Determinant B Induces Rapid Antibody Responses in Rhesus Macaques and Specific Increased Survival in a Murine *S. aureus* Sepsis Model" Infect. Immun. 74:2215 (2006).
Lowy et al., "*Staphylococcus aureus* Infections" 1998, N. Engl. J. Med. 339:520-32.
Mamo et al., "Vaccination with *Staphylococcus aureus* fibrinogen binding proteins FgBPs reduces colonisation of *S. aureus* in a mouse mastitis model" 1994, FEMS Immunol. Med. Microbiol. 10:47-54.
Nandakumar et al., "Proteome Analysis of Membrane and Cell Wall Associated Proteins from *Staphylococcus aureus*" 2005, J. Proteome Res., 4:250-7.
Nilsson et al., "Vaccination with a Recombinant Fragment of Collagen Adhesin Provides Protection against *Staphylococcus Aureus*—mediated Septic Death" 1998, J. Clin. Invest. 101:2640-2649.
Palazzo et al., "First Report of Vancomycin-Resistant *Staphylococci* Isolated from Healthy Carriers in Brazil" 2005, J. Clin. Microbiol. 43:179-85.
Pieper et al., "Comparative proteomic analysis of *Staphylococcus aureus* strains with differences in resistance to the cell wall-targeting antibiotic vancomycin" 2006, Proteomics 6:4246-58.

(Continued)

Primary Examiner — Robert A Zeman
(74) Attorney, Agent, or Firm — Alysia A. Finnegan; Sheldon O. Heber

(57) ABSTRACT

The novel protein SA1789 from *Staphylococcus aureus* is provided as well as nucleic acid and nucleic acid sequence homologues encoding this protein. Also provided is a composition, particularly a *S. aureus* vaccine, comprising SA1789 protein or a fragment or derivative thereof capable of generating an immune response that leads to the killing and clearance of *S. aureus*.

6 Claims, 3 Drawing Sheets

(56) References Cited

OTHER PUBLICATIONS

Selvey et al., "Nosocomial methicillin-resistant *Staphylococcus aureus* bacteremia: is it any worse than nosocomial methicillin-sensitive *Staphylococcus aureus* bacteremia?" 2000, Infect. Control. Hosp. Epidemiol. 21:645-8.

Shinefield et al., "Use of a *Staphylococcus aureus* conjugate vaccine in patients receiving hemodialysis" 2002, N. Eng. J. Med.. 346:491-496.

Tenover et al., 'Characterization of *Staphylococci* with Reduced Susceptibilities to Vancomycin and Other Glycopeptides' 1998, J. Clin. Microbiol. 36:1020-7.

Tenover et al., "Increasing resistance to vancomycin and other glycopeptides in *Staphylococcus aureus*" 2001, Emerg. Infect. Dis. 7:327-32.

Vytvytska et al., "Identification candidate antigens of *Staphylococcus aureus* by serological proteome analysis" 2002, Proteomics 2:580-90.

Weichhart et al., "Functional Selection of Vaccine Candidate Peptides from *Staphylococcus aureus* Whole-Genome Expression Libraries In Vitro" 2003, Infect. Immun. 71:4633-41.

Yang et al., "A novel peptide isolated from phage library to substitute a complex system for a vaccine against *staphylococci* infection" 2006, Vaccine 24:1117-23.

Kuroda et al., "Whole genome sequencing of meticillin-resistant *Staphylococcus aureus*" 2001, Lancet 357:1225-1240.

\* cited by examiner

SA1789 DNA Sequence (489 bp):

ATGGATTGGATTTTACCAATTGCTGGAATTATCGCTGCGATTGCATTCTT
AATTTTATGTATCGGTATCGTAGCTGTATTAAATTCTGTTAAGAAAAACT
TAGATTATGTTGCAAAAACACTTGACGGTGTAGAAGGTCAAGTTCAAGGT
ATTACTCGTGAAACAACAGATTTACTTCATAAAGTAAACCGTTTAACTGA
GGATATCCAAGGTAAAGTAGATCGTTTAAACTCAGTTGTAGATGCTGTTA
AAGGTATCGGTGACTCAGTACAAACGTTAAACAGCTCTGTAGATCGTGTA
ACAAATTCAATTACACATAATATTTCTCAAAATGAAGATAAAATCTCACA
AGTTGTTCAATGGTCAAATGTTGCAATGGAAATTGCAGACAAATGGCAAA
ATAGACACTACCGTCGTGGAAGTGCAAATTACAAAGCTAATAATGTAGCA
ACTGATGCAAATCATAGCTATACTTCTAGAGTAGATAAA (SEQ ID NO: 1)

FIG. 1

STAPHYLOCOCCUS AUREUS SURFACE PROTEIN SA1789 AND PROTECTIVE VACCINE BASED THEREON

CROSS-REFERENCE TO RELATED APPLICATIONS

This application is a §371 National Stage Application of PCT/US2011/43274, international filing date of Jul. 8, 2011, which claims the benefit of U.S. Provisional Application No. 61/363,893, filed Jul. 13, 2010, and U.S. Provisional Application No. 61/366,360, filed Jul. 21, 2010, which are hereby incorporated by reference in their entirety.

REFERENCE TO SEQUENCE LISTING SUBMITTED ELECTRONICALLY

The sequence listing of the present application is submitted electronically via EFS-Web as an ASCII formatted sequence listing with a file name "MRLIFD00030USPCT_SEQLIST_11JAN2013.TXT", creation date of Jan. 11, 2013, and a size of 10.7 KB. This sequence listing submitted via EFS-Web is part of the specification and is herein incorporated by reference in its entirety.

FIELD OF THE INVENTION

The present invention relates to SA1789 protein from *Staphylococcus aureus*, or a fragment, variant or derivative thereof, as well as nucleic acid sequences encoding this protein. The present invention also relates to a composition, particularly a *S. aureus* vaccine, comprising SA1789 protein, or a fragment, variant or derivative thereof, capable of generating an immune response that induces opsonophagocytic activity of human neutrophils for *S. aureus*, as well as methods of use of the composition.

BACKGROUND OF THE INVENTION

*Staphylococcus aureus* is a nosocomial as well as a community-acquired pathogen, which causes a wide range of diseases and conditions, from minor skin infections to serious life-threatening conditions such as bacteraemia, endocarditis, pneumonia, toxic shock syndrome and wound infections. See Lowy et al., 1998, *N. Engl. J. Med.* 339:520-32. Additional examples of diseases and conditions caused by *S. aureus* include botryomyosis, bullous impetigo, carbuncle, cellulitis, central nervous system infections, folliculitis, furuncle, impetigo, infective and inflammatory eye disease, osteomyelitis and other infections of joints and bones, respiratory tract infections, and scalded skin syndrome. See The Staphylococci in Human Disease, Crossley and Archer (eds.), Churchill Livingstone Inc. 1997.

The worldwide growing incidence of staphylococcal infections is strongly related to an increased use of surgical devices and a growing number of immunocompromised patients. The situation has become more serious since the increased use of antibiotics has led to the emergence of methicillin-resistant *S. aureus* strains (MRSA). See Selvey et al., 2000, *Infect. Control. Hosp. Epidemiol.* 21:645-8; Peacock et al., 1980, *Ann. Intern. Med.* 93:526-32. More recently, *S. aureus* isolates with reduced susceptibility to vancomycin, the antibiotic of choice against MRSA strains, and isolates with vancomycin-resistance have been described. See Tenover et al., 2001, *Emerg. Infect. Dis.* 7:327-32; Tenover et al., 1998, *J. Clin. Microbiol.* 36:1020-7; and Palazzo et al., 2005, *J. Clin. Microbial.* 43:179-85. The rising emergence of multidrug-resistant staphylococci has led to a growing interest in the development of alternative approaches to prevent and treat staphylococcal infections.

Examples of polysaccharides that have been employed as possible vaccine components include *S. aureus* type 5 and type 8 capsular polysaccharides. See Shinefield et al., 2002, *N. Eng. J. Med.* 346:491-496. Examples of polypeptides that have been employed as possible vaccine components include clumping factor, collagen adhesin, and fibrinogen binding proteins. See Mamo et al., 1994, *FEMS Immunol. Med. Mic.* 10:47-54; Nilsson et al., 1998, *J. Clin. Invest.* 101:2640-2649; Josefsson et al., 2001, *J. Infect. Dis.* 184:1572-1580.

Much effort has been made in identifying additional *S. aureus* antigens for use in vaccines. Methods for identifying such antigens have included identifying *S. aureus* polypeptide sequences from sequencing the *S. aureus* genome (see Kuroda et al., 2001, *Lancet* 357:1225-1240; Baba et al., 2000, *Lancet* 359:1819-1827; European Patent Publication EP 0786519) including the use of bioinformatics to characterize polypeptide sequences obtained from genome sequencing (see, e.g., European Patent Publication EP 0786519); employing techniques such as those involving display technology and sera from infected patients (see, e.g., International Publication Nos. WO 01/98499 and WO 02/059148; and Etz et al., 2002, *Proc. Natl. Acad. Sci. USA* 99:6573-6578); and technologies, like proteomics (see Brady et al., 2006, *Infect. Immun.*, 74:3415-26; Gatlin et al., 2006, *Proteomics* 6:1530-49; Pieper et al., 2006, *Proteomics* 6:4246-58; Vytvytska et al., 2002, *Proteomics* 2:580-90; Nandakumar et al., 2005, *J. Proteome Res.*, 4:250-7) or protein selection methods based on expression libraries (see Clarke et al., 2006, *J. Infect. Dis.* 193:1098-108; Etz et al., 2002, *Proc. Natl. Acad. Sci. USA* 99:6573-8; Weichhart et al., 2003, *Infect. Immun.* 71:4633-41; and Yang et al., 2006, Vaccine 24:1117-23).

Citation or identification of any reference in this section or any other section of this application shall not be construed as an indication that such reference is available as prior art to the present invention.

SUMMARY OF THE INVENTION

The present invention relates to SA1789 polypeptide, a putative general stress protein, which gene was found present in all tested strains of *S. aureus* and has a predicted molecular weight of about 18 kDa. Accordingly, the present invention provides an isolated polypeptide according to SEQ ID NO: 2 or fragment, variant or derivative thereof, and uses of such polypeptides for the prevention, amelioration and/or treatment of *S. aureus* infections or pathological symptoms thereof in human or non-human mammalian patients. SEQ ID NO: 2 is the full-length SA1789 sequence. A derivative of SEQ ID NO: 2 containing an amino His-tag and three additional carboxylamino acids was found to produce a protective immune response against *S. aureus*.

A first aspect of the invention provides an isolated polypeptide comprising the amino acid sequence of SEQ ID NO: 2, or a fragment, variant or derivative thererof, preferably wherein the polypeptide is not SEQ ID NO: 4. In one embodiment, the polypeptide comprises the amino acid sequence of SEQ ID NO: 2 or is a derivative thereof. In another embodiment, a derivative of SA1789 includes one or more additional regions or moieties covalently joined to the polypeptide, wherein each region or moiety is independently selected from a region or moiety having at least one of the following properties: enhances the immune response, facilitates purification, or facilitates polypeptide stability. In certain embodiments, the additional regions or moieties are covalently joined at the carboxyl terminus or amino terminus. Additional region or moiety indicates a region or moiety different from a *S. aureus* SA1789 polypeptide. The additional region or moiety can be, for example, an additional polypeptide region or a non-peptide region. In one embodiment, a derivative consists of the amino acid sequence of SEQ ID NO: 2 with an N-terminal methionine. In certain embodiments, the polypeptide comprises, or alternatively, consists of, the polypeptide of SEQ ID NO: 2. The polypeptide may be substantially purified. In certain embodiments, the polypeptide provides protective immunity against *S. aureus* when administered to a patient in need thereof.

A second aspect of the invention provides a composition able to induce protective immunity against *S. aureus* in a human or non-human mammalian patient comprising an immunologically effective amount of an SA1789 polypeptide or a fragment, variant or derivative thereof, and a pharmaceutically acceptable carrier. Preferably, said composition is a pharmaceutical and/or immunogenic composition such as a vaccine. An immunologically effective amount is an amount sufficient to provide protective immunity against *S. aureus* infection. The amount should be sufficient to significantly prevent the likelihood or severity of a *S. aureus* infection. In other embodiments, the composition comprises any of the polypeptides described above. In certain embodiments, the composition further comprises an adjuvant.

A third aspect of the invention provides methods of treating and/or preventing *S. aureus* infection in a human or non-human mammalian patient comprising administrating a immunologically effective amount of a composition of the invention to said patient. Said methods induce a protective immune response against *S. aureus* infection in the patient. In one embodiment, the patient is a human. In certain embodiments, the human is immunocompromised. An immunocompromised patient can be an elderly patient, an infant or young child, or a patient with a disease such as AIDS. In alternative embodiments, the patient is a non-human mammal.

A fourth aspect of the invention provides a use of an immunologically effective amount of a polypeptide according to SEQ ID NO: 2, or a fragment, variant or derivative thereof, in the manufacture of a medicament for inducing a protective immune response in a patient against *S. aureus* infection. In one embodiment of this aspect of the invention, the patient is a human. In alternative embodiments, the patient is a non-human mammal.

A fifth aspect of the invention provides an isolated nucleic acid sequence encoding a SA1789 polypeptide or fragment, variant or derivative thereof. In one embodiment, the sequence is the nucleotide sequence of SEQ ID NO: 1.

A sixth aspect of the invention provides an expression vector comprising a nucleic acid sequence in the fifth aspect wherein said sequence is operably linked to transcriptional and translational regulatory nucleic acid.

A seventh aspect of the invention provides a host cell containing an expression vector of the invention.

An eighth aspect of the invention provides a method of producing a recombinant SA1789 polypeptide, said method comprising the steps of: (a) culturing a host cell containing an expression vector comprising a DNA sequence of SEQ ID NO: 1 such that said recombinant polypeptide is expressed from said nucleic acid; and (b) isolating said recombinant polypeptide. In other embodiments, the method produces any of the polypeptides described above.

BRIEF DESCRIPTION OF THE DRAWINGS

FIG. 1 shows the DNA sequence of SA1789 (SEQ ID NO:1).

DETAILED DESCRIPTION OF THE INVENTION

Figure 2:
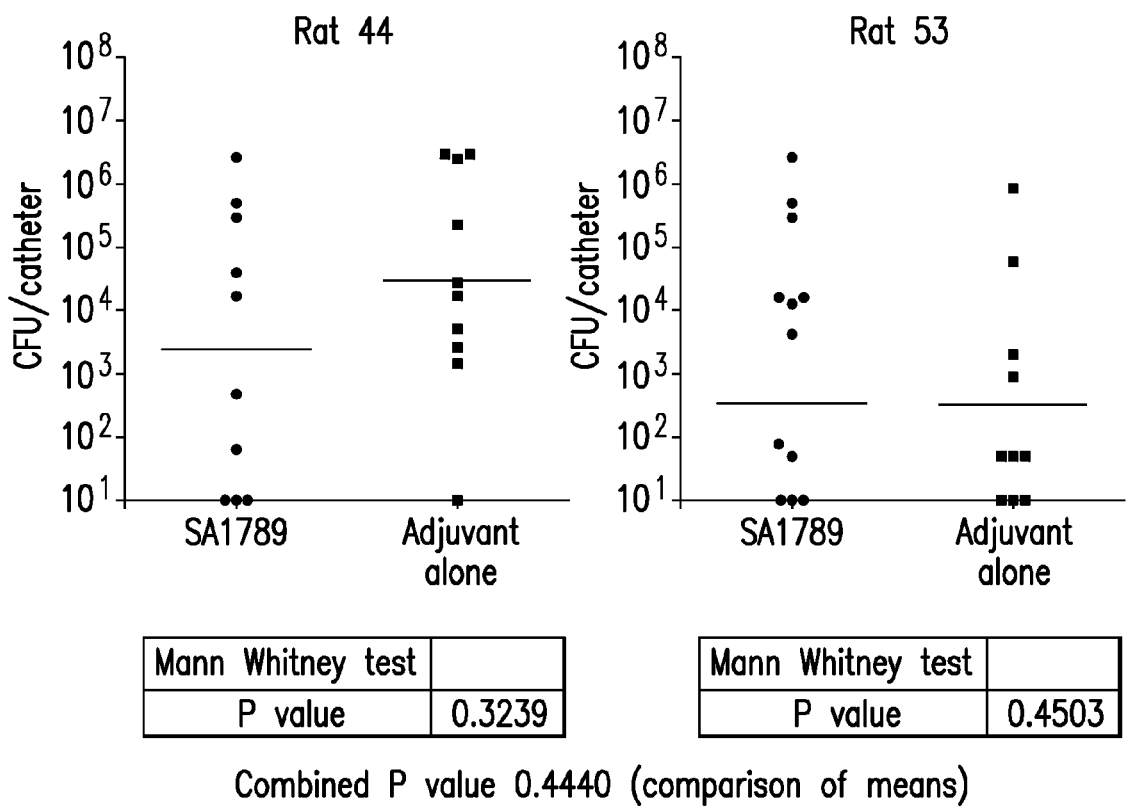
FIG. 2 shows the protective effect of SA1789 when used to immunize rats, in an indwelling catheter model. Rats were immunized with either SEQ ID NO:3 adsorbed onto amorphous aluminum hydroxyphosphate sulfate adjuvant (SA1789+AAHSA) or adjuvant alone (AAHSA) and then challenged with *S. aureus* via the tail vein (see Example 4). Catheters were removed and evaluated for *S. aureus* colonization after 24 hours.
Figure 3A:
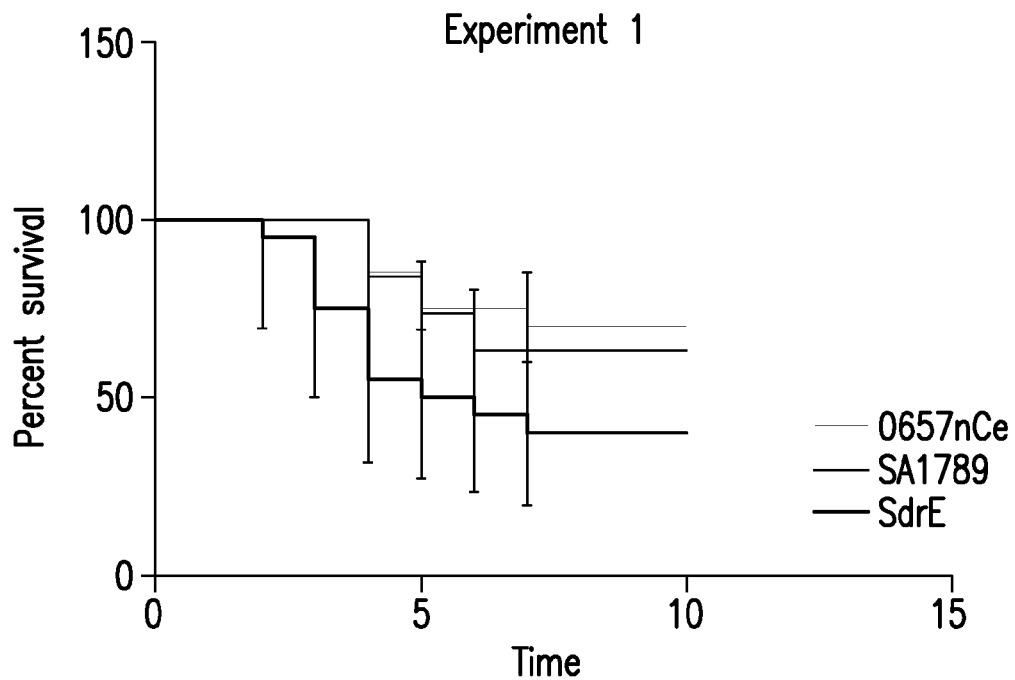
FIG. 3 shows the protective effect of SA1789 when used to immunize mice, in a lethal challenge model. Two separate experiments were performed (panels A and B) in which Balb/c mice were immunized with SA1789 or BSA (negative control) and then challenged with a lethal does of *S. aureus* Becker via the tail vein (see Example 5). Survival was monitored for 10 days post challenge ("time," x-axis).
Figure 3B:
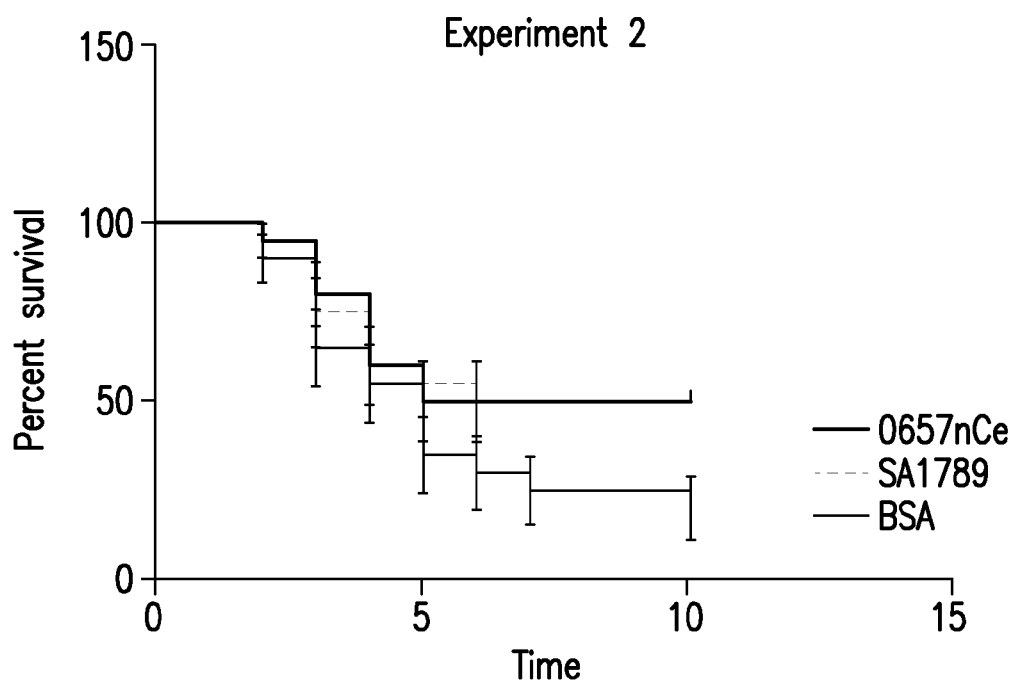

The present invention is based at least in part, on the identification of SA1789, a conserved protein, using a proteomics approach. SA1789 is expressed during times when the critical nutrient, iron, is available in extremely limited quantity. This situation is reflective of the internal human environment. Therefore, SA1789 is expressed during infection of the human body, and allows stimulation of the immune system, for clearance of bacteria.

Reference to a SA1789 polypeptide refers to a polypeptide that produces a protective immune response that recognizes the SA 1789 protein in *S. aureus*. In different embodiments, the SA1789 protein in *S. aureus* recognizes at least one or more of the following strains: COL, Becker. MW2, N315, Newman, USA300.

SEQ ID NO: 2 represents the full-length protein sequence of the *S. aureus* SA1789 antigen. A derivative of SEQ ID NO: 2 containing an $NH_2$-terminal histidine-tag ("his-tag") and three additional carboxyl amino acids (SEQ ID NO: 3) was found to produce a protective immune response against *S. aureus*. The his-tag facilitates polypeptide purification and identification.

In additional embodiments, the SA1789 polypeptide comprises a polypeptide region, the region is at least 90%, at least 94%, at least 95% or at least 99% identical to SEQ ID NO: 2; differs from SEQ ID NO: 2 by 0, 1, 2, 3, 4, 5, 6, 7, 8, 9, 10, 11, 12, 13, 14, 15, 16, 17, 18, 19, 20, 21, 22, 23, 24, or 25 alterations, or up to 50 alterations; or consists essentially or consists of such a region. Examples of alterations includes amino acid substitutions, deletions, and insertions.

Accordingly, the present invention provides an isolated polypeptide according to SEQ ID NOs: 2, or a fragment, variant or derivative thereof. In one embodiment, the polypeptide, fragments, variants and derivatives of the invention elicit an immune response against *S. aureus*.

The invention also provides a DNA sequence encoding a polypeptide of the invention, e.g., SEQ ID NO: 1, and expression vectors comprising said DNA sequences. The present invention also provides a host cell comprising an expression vector comprising the DNA sequence of SEQ ID NO: 1. The host cell may be any suitable prokaryotic or eukaryotic cell. In one embodiment, the host cells are prokaryotic cells such as *E. coli*. The present invention also provides method of producing SA1789 comprising culturing the host cell and collecting the desired protein from the host cell or the culture broth.

The invention also provides antibodies against the SA1789 protein. Such antibodies can be prepared (i.e., raised against the antigen) by suitable methods known to a skilled person.

Among the uses for SA1789 is use as a vaccine for the prevention of staphylococcal infections and as a target for generating a monoclonal antibody for the prevention or treatment of staphylococcal infections.

The present invention includes one or more of the polypeptide immunogens or compositions thereof, described herein, or a vaccine comprising or consisting of said immunogens or compositions (i) for use in, (ii) for use as a medicament for, or (iii) for use in the preparation of a medicament for: (a) therapy (e.g., of the human body); (b) medicine; (c) inhibition of *S. aureus* replication; (d) treatment or prophylaxis of infection by *S. aureus*; or, (e) treatment, prophylaxis of, or delay in the onset or progression of *S. aureus*-associated disease(s). In these uses, the polypeptide immunogens, compositions thereof, and/or vaccines comprising or consisting of said immunogens or compositions can optionally be employed in combination with one or more anti-bacterial agents (e.g., anti-bacterial compounds; combination vaccines, described infra).

As used herein, the phrase "consists essentially of" when used in connection with a polypeptide, e.g., the SA1789 polypeptide, indicates that the referred to amino acids (from the SEQ ID NO) are present and additional amino acids may be present. The additional amino acids can be at the carboxyl terminus, the amino terminus or a combination of the two. In different embodiments 1, 2, 3, 4, 5, 6, 7, 8, 9, 10, 11, 12, 13, 14, 15, 16, 17, 18, 19, or 20 additional amino acids are present. In preferred embodiments methionine is present at the amino terminus; or methionine-glycine is present at the amino terminus.

As used herein, the term "derivative" refers to a polypeptide having one or more alterations, which can be an additional amino acid or a chemical modification. In different embodiments, the SEQ ID NO: 2-related polypeptide differs from SEQ ID NO: 2 by 1, 2, 3, 4, 5, 6, 7, 8, 9, 10, 11, 12, 13, 14, 15, 16, 17, 18, 19, or 20 amino acid additions. A preferred additional amino acid is an amino-terminal methionine. The term "derivative" also encompasses chemical modifications of the protein (e.g., the modification of functional groups), linking of functional groups (such as alkylation, hydroxylation, phosphatation, thiolation, carboxilation and the like), linkage to at least one further functional protein domain (such as marker proteins, carrier proteins, proteins holding adjuvant properties and the like; the linkage being directly or via a linker molecule) and to other biologically active molecules (toxins, antibiotics, lipids, carbohydrates, nucleic acids and the like). In some embodiments, a derivative may have up to 50, 100, or 200 additional amino acids.

As used herein, the phrase "elicit(s) an immune response" refers to the ability of a SA1789 polypeptide, or fragment, variant or derivative thereof, to produce an immune response in a mammal to which it is administered, wherein the response includes the production of elements, such as antibodies, which specifically bind *S. aureus* and/or said polypeptide, fragment, variant or derivative, and/or which provide a protective effect against *S. aureus* infection.

As used herein, the term "fragment" refers to a continuous segment of the SA1789 polypeptide having at least 10 amino acid residues and which is shorter than the full-length SA1789 polypeptide. The term includes deletion mutants and small peptides, for example of at least 10 and more preferably at least 20 amino acids in length, which comprise antigenic determinants or epitopes. One or more of such fragments may be joined together. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and staphylococcins V8-protease. The digested fragments can be purified by, for example, high performance liquid chromatographic (HPLC) techniques.

As used herein, the term "immunologically effective amount" means a sufficient amount of a composition that, when introduced into a patient, results in an immune response against *S. aureus*. One skilled in the art recognizes that this level may vary. The amount should be sufficient to significantly prevent and/or reduce the likelihood or severity of a *S. aureus* infection.

As used herein, the term "isolated" indicates a different form than found in nature. The different form can be, for example, a different purity than found in nature. In one embodiment, the term refers to material that is substantially or essentially free from components that normally accompany it in its native state.

As used herein, the term "operably linked" means that the transcriptional and translational regulatory nucleic acid is positioned relative to the nucleotide sequence encoding the said polypeptide, fragment, variant or derivative in such a manner that such transcription is initiable. The transcriptional and translational regulatory nucleic acid will generally be appropriate for the host cell used for expression. Numerous types of appropriate expression vectors and suitable regulatory sequences are known in the art for a variety of host cells.

As used herein, the terms "prevention" or "prevent" refers to one or more of the following effects: reduce susceptibility to *S. aureus* infection, reduce the ability of the infecting bacterium to establish persistent infection for chronic disease, reduce the ability of *S. aureus* to propagate in an infected patient, reduce the amount of *S. aureus* in an infected patient, or reduce the likelihood of recurrence of *S. aureus* infection.

As used herein, the term "protective" immunity or immune response, when used in the context of a polypeptide, immunogen and/or treatment method described herein, indicates a detectable level of protection against *S. aureus* infection. This includes therapeutic and/or prophylactic measures reducing the likelihood of *S. aureus* infection or of obtaining a disorder(s) resulting from such infection, as well as reducing the severity of the infection and/or a disorder(s) resulting from such infection. As such, a protective immune response includes, for example, the ability to reduce bacterial load, ameliorate one or more disorders or symptoms associated with said bacterial infection, delaying the onset of disease progression resulting from S. aureus infection and/or reducing the likelihood of recurrence of S. aureus infection.

The level of protection can be assessed using animal models such as those known to those skilled in the art. For example, certain polypeptides described herein provide protection in both a murine, lethal-challenge model (see, e.g., Thakker et al., 1998, *Inf Immun* 66:5183-5189; Fattom et al., 1996, *Inf Immun* 64:1659-1665) and a rat, indwelling-catheter, sub-lethal challenge model (see, e.g., Ulphani et al., 1999, *Lab Animal Sc.* 49:283-287; Baddour et al., 1992, *J Inf Dis* 165:749-53; Ebert et al., *Human Vaccines* 7(6): 1-9 (2011)).

As used herein, the term "protein" or "polypeptide," used interchangeably herein, indicates a contiguous amino acid sequence and does not provide a minimum or maximum size limitation. One or more amino acids present in the protein may contain a post-translational modification from a host cell, such as a yeast host, such as glycosylation or disulfide bond formation.

As used herein, the terms "purified" with regard to, for example, a polypeptide immunogen indicates the presence of such polypeptide in an environment lacking one or more other polypeptides with which it is naturally associated and/or is represented by at least about 10% of the total protein present. In different embodiments, the purified polypeptide represents at least about 50%, at least about 75%, or at least about 95% of the total protein in a sample or preparation.

As used herein, "recombinant polypeptide" is meant a polypeptide made using recombinant techniques, i.e., through the expression of a recombinant nucleic acid.

As used herein, the term "recombinant nucleic acid" refers to nucleic acid formed in vitro by the manipulation of nucleic acid into a form not normally found in nature. In this regard, the recombinant nucleic acid preferably comprises an expression vector that may be either a self-replicating extra-chromosomal vector such as a plasmid, or a vector that integrates into a host genome. Generally, such expression vectors include transcriptional and translational regulatory nucleic acid operably linked to the said nucleotide sequence.

As used herein, the term "substantially purified" with regard to, for example, a polypeptide immunogen indicates the presence of such polypeptide in an environment lacking all, or most, other polypeptides with which the polypeptide is naturally associated. For example, a substantially purified S. aureus polypeptide is present in an environment lacking all, or most, other S. aureus polypeptides. An environment can be, for example, a sample or preparation.

As used herein, the term "variant" refers to polypeptides in which one or more amino acids have been replaced by different amino acids. It is well understood in the art that some amino acids may be changed to others with broadly similar properties without changing the nature of the activity of the polypeptide (conservative substitutions). The term "variant" also includes naturally occurring allelic variants.

Polypeptide Sequences

S. aureus SA1789 is a conserved surface protein having an amino acid sequence as set forth in SEQ ID NO: 2. SEQ ID NO: 2 corresponds to the about 18 kDa surface polypeptide of the obtained from S. aureus COL strain. The native protein sequence is as follows:

```
  1 VLNSVKKNLD YVAKTLDGVE GQVQGITRET TDLLHKVNRL TEDIQGKVDR
 51 LNSVVDAVKG IGDSVQTLNS SVDRVTNSIT HNISQNEDKI SQVVQWSNVA
101 MEIADKWQNR HYRRGSANYK ANNVATDANH SYTSRVDK
```

In certain embodiments of the invention, there is an amino-terminal methionine to facilitate translation.

SEQ ID NO: 3 corresponds to the SA1789 polypeptide having an amino terminal His-tag and three additional amino acids at the carboxy terminus (all additional amino acids are underlined). The amino acid sequence is as follows:

```
  1 MGHHHHHHHH HHSSGHIEGR HMVLNSVKKN LDYVAKTLDG VEGQVQGITR
 51 ETTDLLHKVN RLTEDIQGKV DRLNSVVDAV KGIGDSVQTL NSSVDRVTNS
101 ITHNISQNED KISQVVQWSN VAMEIADKWQ NRHYRRGSAN YKANNVATDA
151 NHSYTSRVDK AEQ
```

Preferably, the polypeptide, or a fragment, variant or derivative thereof, is purified or isolated. In an embodiment, the polypeptide is substantially purified. Reference to "purified" or "substantially purified" does not require a polypeptide to undergo any purification and may include, for example, a chemically synthesized polypeptide that has not been purified.

The use of the terms "fragments", "variants" and "derivatives" is not mutually exclusive. In other words, a fragment can have additions and/or substitutions, a variant can have deletions and/or additions, and a derivative can have deletions and/or substitutions.

Derivatives

In an embodiment of the present invention, a derivative of SA1789 contains one or more additional regions or moieties covalently joined to the polypeptide, wherein each region or moiety is independently selected from a region or moiety having at least one of the following properties: facilitates polypeptide production, facilitates purification, or facilitates polypeptide stability or enhances the immune response. Such additional regions or moieties can be covalently joined to the polypeptide through the carboxyl terminus, amino terminus or an internal region of the protein. Derivatives include additions to polypeptides according to SEQ ID NOS: 2, or variants thereof, wherein said derivatives retain activity eliciting an immune response. "Additions" of amino acids may include fusion of the polypeptides or variants thereof with other polypeptides or proteins. In different embodiments, 1, 2, 3, 4, 5, 6, 7, 8, 9, 10, 11, 12, 13, 14, 15, 16, 17, 18, 19, or 20 amino acids are added. In other embodiments at least 1, 2, 3, 4, 5, 6, 7, 8, 9, 10, 11, 12, 13, 14, 15, 16, 17, 18, 19, or 20 amino acids are added. In some embodiments, an upper limit of 30, 35, 40, 45, 50, 55, 60, 65, 70, 75, 80, 85, 90, 95 or 100 amino acids is added.

In one embodiment, a derivative of SEQ ID NO: 2 does not have the amino acid sequence of SEQ ID NO: 4.

Exemplary conservative substitutions in the polypeptide may be made according to the following table:

TABLE 1

| ALIPHATIC | Non-polar | G A P |
|           |           | I L V |
|           | Polar—uncharged | C S T M |
|           |           | N Q |
|           | Polar—charged | D E |
|           |           | K R |
| AROMATIC  |           | H F W Y |

Generally, the substitutions which are likely to produce the greatest changes in a polypeptide's properties are those in

```
  1 MDWILPIAGI IAAIAFLILC IGIVAVLNSV KKNLDYVAKT LDGVEGQVQG

51 ITRETTDLLH KVNRLTEDIQ GKVDRLNSVV DAVKGIGDSV QTLNSSVDRV

101 TNSITHNISQ NEDKISQVVQ WSNVAMEIAD KWQNRHYRRG SANYKANNVA

151 TDANHSYTSR VDK
```

For example, polypeptide production can be facilitated through the use of an initiation codon (e.g., coding for methionine) suitable for recombinant expression. The methionine may be later removed during cellular processing.

For example, polypeptide purification can be facilitated by adding a group to the carboxyl or amino terminus to facilitate purification. Examples of groups that can be used to facilitate purification include polypeptides providing affinity tags. Examples of affinity tags include a six-histidine-tag, trpE, glutathione and maltose-binding protein.

For example, polypeptide stability can be enhanced by using groups such as polyethylene glycol that may be present on the amino or carboxyl terminus.

An immune response can be enhanced by making the derivative more effective against S. aureus or by producing an immune response against another pathogen. Fusion proteins can be added which produce an immunomodulatory response. Particular examples of such proteins include Protein A or glutathione S-transferase (GST).

The ability of a polypeptide to produce an immune response can be improved using groups that generally enhance an immune response. Examples of groups that can be joined to a polypeptide to enhance an immune response against the polypeptide include cytokines such as IL-2 (Buchan et al., 2000, Molecular Immunology 37:545-552).

Variants

Variants of SA1789 include polypeptides having amino acid substitutions. In different embodiments 1, 2, 3, 4, 5, 6, 7, 8, 9, 10, 11, 12, 13, 14, 15, 16, 17, 18, 19, or 20 amino acids are substituted. Substitutions may be desirable, for example, to facilitate cloning by introducing restriction sites through amino acid changes.

Generally, in substituting different amino acids to retain activity it is preferable to exchange amino acids having similar properties. Factors that can be taken into account for an amino acid substitution include amino acid size, charge, polarity, and hydrophobicity. The effect of different amino acid R-groups on amino acid properties are well known in the art. (See, for example, Ausubel, Current Protocols in Molecular Biology, John Wiley, 1987-2002, Appendix 1C.)

For example, substituting valine for leucine, arginine for lysine, and asparagine for glutamine are good candidates for not causing a change in polypeptide functioning.

which (a) a hydrophilic residue (e.g., Ser or Thr) is substituted for, or by, a hydrophobic residue (e.g., Ala, Len, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser) or no side chain (e.g., Gly).

Nucleic acids encoding polypeptides according to the invention, e.g., SEQ ID NOS: 2 and 3, can be mutated using either random mutagenesis, for example using transposon mutagenesis, or site-directed mutagenesis. The resultant DNA fragments are then cloned into suitable expression hosts such as E. coli using conventional technology and clones that retain the desired activity are detected. Where the clones have been derived using random mutagenesis techniques, positive clones would have to be sequenced in order to detect the mutation.

Efficacy of a polypeptide to induce a protective immune response can be improved through epitope enhancement. Epitope enhancement can be performed using different techniques such as those involving alteration of anchor residues to improve peptide affinity for MHC molecules and those that increase the affinity of the peptide-MHC complex for a T-cell receptor. See Berzofsky et al., 2001, Nature Review 1:209-219.

It may also be desirable to incorporate unnatural amino acids and derivatives to improve the properties on the polypeptides of the invention. Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. Unnatural amino acids include those known to one skilled in the art.

Polypeptide Production

Polypeptides can be produced using standard techniques including those involving chemical synthesis and those involving purification from a cell producing the polypeptide. Techniques for chemical synthesis of polypeptides are well known in the art. See, e.g., Vincent, *Peptide and Protein Drug*

Delivery, New York, N.Y., Decker, 1990. Techniques for recombinant gene production, introduction into a cell, and recombinant gene expression are well known in the art. Examples of such techniques are provided in references such as Ausubel, *Current Protocols in Molecular Biology*, John Wiley, 1987-2002; and Sambrook et al., *Molecular Cloning, A Laboratory Manual*, 2$^{nd}$ Edition, Cold Spring Harbor Laboratory Press, 1989; and Coligan et al., Current Protocols in Protein Science (John Wiley & Sons, Inc. 1995-1997).

Obtaining polypeptides from a cell is facilitated by using recombinant nucleic acid techniques to produce the polypeptide. Recombinant nucleic acid techniques for producing a polypeptide involve introducing, or producing, a recombinant gene encoding the polypeptide in a cell and expressing the polypeptide.

A recombinant gene contains a nucleic acid that encodes a polypeptide, along with regulatory elements for polypeptide expression. The recombinant gene can be present in a cellular genome or can be part of an expression vector.

The regulatory elements that may be present as part of a recombinant gene include those naturally associated with the polypeptide-encoding sequence, as well as exogenous regulatory elements not naturally associated with the polypeptide-encoding sequence. Typically, the transcriptional and translational regulatory nucleic acid may include, but is not limited to, promoter sequences, leader or signal sequences, ribosomal binding sites, transcriptional start and stop sequences, translational start and stop sequences, and enhancer or activator sequences. Exogenous regulatory elements, such as an exogenous promoter, can be useful for expressing a recombinant gene in a particular host or for increasing the level of expression. Generally, the regulatory elements that are present in a recombinant gene include at a minimum a transcriptional promoter, a ribosome binding site, a transcriptional terminator, and an optionally present operator. A preferred element for processing in eukaryotic cells is a polyadenylation signal.

Constitutive or inducible promoters as known in the art are contemplated by the invention. The promoters may be either naturally occurring promoters, or hybrid promoters that combine elements of more than one promoter.

Expression of a recombinant gene in a cell is facilitated through the use of an expression vector. In addition to a recombinant gene, an expression vector usually contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. In a preferred embodiment, the expression vector contains a selectable marker gene to allow the selection of transformed host cells. Selection genes are well known in the art and will vary with the host cell used.

Recombinant polypeptides of the invention may be produced by culturing a host cell transformed with an expression vector containing nucleic acid encoding a polypeptide, fragment, variant or derivative according to the invention. The conditions appropriate for protein expression will vary with the choice of expression vector and the host cell. This is easily ascertained by one skilled in the art through routine experimentation. For example, the polypeptides may be prepared by a procedure including the steps of:

(a) preparing a recombinant nucleic acid containing a nucleotide sequence encoding a polypeptide according to the invention, e.g., SEQ ID NOS: 2 or 3, or fragment thereof, or variant or derivative of these, which nucleotide sequence is operably linked to transcriptional and translational regulatory nucleic acid;

(b) transfecting or transforming a suitable host cell with the recombinant nucleic acid;

(c) culturing the host cell to express recombinant polypeptide from said recombinant nucleic acid; and (d) isolating the recombinant polypeptide.

In one embodiment, the nucleotide sequence is SEQ ID NO: 1.

Suitable cells for recombinant nucleic acid expression of SEQ ID NO: 2-related polypeptides are prokaryotes and eukaryotes. Examples of prokaryotic cells include *E. coli*; members of the *Staphylococcus* genus, such as *S. aureus* and *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *P. fluorescens*. Examples of eukaryotic cells include mammalian cells; insect cells; and yeast cells, such as members of the *Saccharomyces* genus (e.g., *S. cerevisiae*), members of the *Pichia* genus (e.g., *P. pastoris*), members of the *Hansenula* genus (e.g., *H. polymorpha*), members of the *Kluyveromyces* genus (e.g., *K lactis* or *K. fragilis*) and members of the *Schizosaccharomyces* genus (e.g., *S. pombe*).

Alternatively, the host cell may be an insect cell such as, for example, SF9 cells that may be utilized with a baculovirus expression system.

Due to the degeneracy of the genetic code, a large number of different encoding nucleic acid sequences can be used to code for a particular polypeptide. The degeneracy of the genetic code arises because almost all amino acids are encoded by different combinations of nucleotide triplets or "codons." Naturally occurring amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU If desired, expression in a particular host can be enhanced through codon optimization. Codon optimization includes use of more preferred codons. Techniques for codon optimization in different hosts are well known in the art.

SEQ ID NO: 2-related polypeptides may contain post translational modifications, for example, N-linked glycosylation, O-linked glycosylation, or acetylation. Reference to "polypeptide" or an "amino acid" sequence of a polypeptide includes polypeptides containing one or more amino acids having a structure of a post-translational modification from a host cell, such as a yeast host.

Post translational modifications can be produced chemically or by making use of suitable hosts. For example, in *S. cerevisiae* the nature of the penultimate amino acid appears to determine whether the N-terminal methionine is removed. Furthermore, the nature of the penultimate amino acid also determines whether the N-terminal amino acid is N'-acetylated (Huang et al., 1987, *Biochemistry* 26: 8242-8246). Another example includes a polypeptide targeted for secretion due to the presence of a secretory leader (e.g., signal peptide), where the protein is modified by N-linked or O-linked glycosylation (Kukuruzinska et al., 1987, *Ann. Rev. Biochem.* 56:915-944). The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a nucleotide sequence according to the invention into the expression vector so that the translational reading frames of the fusion partner and the nucleotide sequence of the invention coincide.

Well known examples of fusion partners include, but are not limited to, glutathione-S-transferase (GST), Fc portion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention.

Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, influenza virus haemagglutinin and FLAG tags.

Chemical Modifications

Polypeptide stability can be enhanced by modifying the polypeptide carboxyl or amino terminus. Examples of possible modifications include amino terminus protecting groups such as acetyl, propyl, succinyl, benzyl, benzyloxycarbonyl or t-butyloxycarbonyl; and carboxyl terminus protecting groups such as amide, methylamide, and ethylamide.

Side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

The invention also contemplates covalently modifying a polypeptide, fragment or variant of the invention with dinitrophenol, in order to render it immunogenic in humans.

Generation of Antibodies

A SEQ ID NO: 2-related polypeptide can be used to generate antibodies and antibody fragments binding to the polypeptide or to *S. aureus*. Such antibodies and antibody fragments have different uses including use in polypeptide purification, *S. aureus* identification, or in therapeutic or prophylactic treatment against *S. aureus* infection.

Antibodies can be polyclonal or monoclonal. Techniques for producing and using antibodies, including human antibodies, are well known in the art (see, e.g., Ausubel, *Current Protocols in Molecular Biology*, John Wiley, 1987-2002; Harlow et al., *Antibodies, A Laboratory Manual*, Cold Spring Harbor Laboratory, 1988; Kohler et al., 1975, *Nature* 256: 495-497; Azzazy et al., 2002, *Clinical Biochem.* 35:425-445; Berger et al., 2002, *Am. J. Med. Sci.* 324:14-40).

Techniques for generating antigen binding protein such as a single-chain antibody, an antibody, or an antibody fragment are well known in the art. Examples of such techniques include the use of phage display technology, identification and humanization of rodent antibodies, and generation of human antibodies using a XenoMouse or Trans-Chromo mouse. See, e.g., Azzazy et al., 2002, *Clinical Biochemistry* 35:425-445; Berger et al., 2002, *Am. J. Med. Sci.* 324:14-40.

Murine antibodies can be humanized, and CDR's, can be grafted onto human antibody frameworks using techniques well known in art. Such techniques are generally described with reference to humanizing murine antibodies by grafting murine variable regions onto a human antibody framework and, if needed making further modifications. See, e.g., O'Brien et al., Humanization of Monoclonal Antibodies by CDR Grafting, p 81-100, From Methods in Molecular Biology Vol 207: Recombinant antibodies for Cancer Therapy: Methods and Protocols (Eds. Welschof and Krauss) Humana Press, Totowa, N.J., 2003.

Antigen binding protein are preferably produced using recombinant nucleic acid techniques or through the use of a hybridoma. Recombinant nucleic acid techniques involve constructing a nucleic acid template for protein synthesis. A hybridoma is an immortalized cell line producing the antigen binding protein.

Recombinant nucleic acid encoding an antigen binding protein can be expressed in a host cell that in effect serves as a factory for the encoded protein. The recombinant nucleic acid can provide a recombinant gene encoding the antigen binding protein that exists autonomously from a host cell genome or as part of the host cell genome.

A recombinant gene contains nucleic acid encoding a protein along with regulatory elements for protein expression. Generally, the regulatory elements that are present in a recombinant gene include a transcriptional promoter, a ribosome binding site, a terminator, and an optionally present operator. A preferred element for processing in eukaryotic cells is a polyadenylation signal. Antibody associated introns may also be present. Examples of expression cassettes for antibody or antibody fragment production are well known in art. See, e.g., Persic et al., 1997, *Gene* 187:9-18; Boel et al., 2000, *J. Immunol. Methods* 239:153-166; Liang et al., 2001, *J. Immunol. Methods* 247:119-130.

Expression of a recombinant gene in a cell is facilitated using an expression vector. Preferably, an expression vector, in addition to a recombinant gene, also contains an origin of replication for autonomous replication in a host cell, a selectable marker, a limited number of useful restriction enzyme sites, and a potential for high copy number. Examples of expression vectors for antibody and antibody fragment production are well known in art. See, e.g., Persic et al., 1997, *Gene* 187:9-18; Boel et al., 2000, *J. Immunol. Methods* 239: 153-166; Liang et al., 2001, *J. Immunol. Methods* 247:119-130.

If desired, nucleic acid encoding an antibody may be integrated into the host chromosome using techniques well known in the art. See, Ausubel, Current Protocols in Molecular Biology, John Wiley, 1987-1998, Mark et al., U.S. Pat. No. 6,743,622.

A variety of different cell lines can be used for recombinant antigen binding protein expression, including those from prokaryotic organisms (e.g., *E. coli, Bacilli, and Streptomyces*) and from Eukaryotic (e.g., yeast, Baculovirus, and mammalian). See Breitling et al., Recombinant Antibodies, John Wiley & Sons, Inc. and Spektrum Akademischer Verlag, 1999.

Preferred hosts for recombinant antigen binding protein expression are mammalian cells able to produce antigen binding protein with proper post translational modifications. Post translational modifications include disulfide bond formation and glycosylation. Another type of post translational modification is signal peptide cleavage.

Proper glycosylation can be important for antibody function. See Yoo et al., 2002, *J. Immunol. Methods* 261:1-20; Li et al., 2006, *Nature Biotechno.* 24:210-215. Naturally occurring antibodies contain at least one N-linked carbohydrate attached to a heavy chain. See Yoo et al., 2002, *J. Immunol. Methods* 261:1-20. Additional N-linked carbohydrates and O-linked carbohydrates may be present and may be important for antibody function. See Yoo et al., 2002, *J. Immunol. Methods* 261:1-20.

Different types of host cells can be used to provide for efficient post-translational modifications including mammalian host cells and non-mammalian cells. Examples of mammalian host cells include Chinese hamster ovary (CHO), HeLa, C6, PC12, and myeloma cells. See Yoo et al., 2002, *J. Immunol. Methods* 261:1-20; Persic et al., 1997, *Gene* 187: 9-18. Non-mammalian cells can be modified to replicate human glycosylation. See Li et al., 2006, *Nature Biotechno.* 24:210-215. Glycoengineered *Pichia pastoris* is an example of such a modified non-mammalian cell. See Li et al., 2006, *Nature Biotechnol.* 24:210-215.

In lieu of the polyclonal antisera obtained in the production species, monoclonal antibodies may be produced using the standard method as for example, described in an article by Kohler and Milstein (1975, *Nature* 256, 495-497) which is herein incorporated by reference, or by more recent modifications thereof as for example, described in Coligan et al., Current Protocols in Protein Science (John Wiley & Sons, Inc. 1995-1997) by immortalizing spleen or other antibody producing cells derived from a production species which has been inoculated with one or more of the polypeptides, fragments, variants or derivatives of the invention.

A hybridoma can be produced using techniques such as those described in Ausubel, Current Protocols in Molecular Biology, John Wiley, 1987-1998, Harlow et al., Antibodies, A Laboratory Manual, Cold Spring Harbor Laboratory, 1988, and Kohler et al., *Nature* 256, 495-497, 1975.

The invention also includes within its scope antibodies which comprise Fc or Fab fragments of the polyclonal or monoclonal antibodies referred to above. Alternatively, the antibodies may comprise single chain Fv antibodies (scFvs) against the peptides of the invention. Such scFvs may be prepared, for example, in accordance with the methods described respectively in U.S. Pat. No. 5,091,513, European Patent No. 239,400 or as described in Winter et al. (1991, *Nature* 349:293).

Pharmaceutical Compositions

A further feature of the invention is the use of the polypeptide, fragment, variant or derivative of the invention ("immunogenic agents") as actives in a composition, preferably an immunogenic composition or vaccine, for protecting patients against infection by *S. aureus*. Suitably, the composition comprises a pharmaceutically acceptable carrier.

By "pharmaceutically-acceptable carrier" is meant a solid or liquid filler, diluent or encapsulating substance that may be safely used in systemic administration. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions including phosphate buffered saline, emulsifiers, isotonic saline, and pyrogen-free water. In particular, pharmaceutically acceptable carriers may contain different components such as a buffer, sterile water for injection, normal saline or phosphate-buffered saline, sucrose, histidine, salts and polysorbate. Terms such as "physiologically acceptable", "diluent" or "excipient" can be used interchangeably.

Compositions of the present invention suitable for oral or parenteral administration may be presented as discrete units such as capsules, sachets or tablets each containing a predetermined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be used as therapeutic or prophylactic vaccines. Accordingly, the invention extends to the production of vaccines containing as actives one or more of the immunogenic agents of the invention. Any suitable procedure is contemplated for producing such vaccines. Exemplary procedures include, for example, those described in New Generation Vaccines (1997, Levine et al., Marcel Dekker, Inc. New York, Basel, Hong Kong), which is incorporated herein by reference.

A peptide of the invention can be conjugated with an immunogenic carrier. Useful carriers are well known in the art and include for example: thyroglobulin; albumins such as human serum albumin; toxins, toxoids or any mutant cross-reactive material (CRM) of the toxin from tetanus, diptheria, pertussis, *Pseudomonas, E. coli, Staphylococcus,* and *Streprococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a peptide of the invention can be coupled to a T cell epitope of a bacterial toxin, toxoid or CRM. In this regard, reference may be made to U.S. Pat. No. 5,785,973, which is incorporated herein by reference.

In addition, a polypeptide, fragment, variant or derivative of the invention may act as a carrier protein in vaccine compositions directed against *S. aureus*, or against other bacteria or viruses.

In a further embodiment, the nucleotide sequence may be used as a vaccine in the form of a "naked DNA" vaccine as is known in the art. For example, an expression vector of the invention may be introduced into a mammal, where it causes production of a polypeptide in vivo, against which the host mounts an immune response as for example described in Barry et al. (1995, *Nature* 377:632-635).

These dosage forms may also include injecting or implanting controlled releasing devices designed specifically for this purpose or other forms of implants modified to act additionally in this fashion. Controlled release of the therapeutic agent may be affected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be affected by using other polymer matrices, liposomes and/or microspheres.

Adjuvants

Adjuvants are substances that can assist an immunogen (e.g., a polypeptide, pharmaceutical composition containing a polypeptide) in producing an immune response. Adjuvants can function by different mechanisms such as one or more of the following: increasing the antigen biologic or immunologic half-life; improving antigen delivery to antigen-presenting cells; improving antigen processing and presentation by antigen-presenting cells; and, inducing production of immunomodulatory cytokines. See Vogel, *Clinical Infectious Diseases* 30 (suppl. 3):S266-270, 2000. In one embodiment of the present invention, an adjuvant is used.

A variety of different types of adjuvants, which are known to those skilled in the art, can be employed to assist in the production of an immune response. Examples of particular adjuvants include aluminum hydroxide; aluminum phosphate, aluminum hydroxyphosphate sulfate or other salts of aluminum; calcium phosphate; DNA CpG motifs; monophosphoryl lipid A; cholera toxin; *E. coli* heat-labile toxin; pertussis toxin; muramyl dipeptide; Freund's incomplete adjuvant; MF59; SAF; immunostimulatory complexes; liposomes; biodegradable microspheres; saponins; nonionic block copolymers; muramyl peptide analogues; polyphosphazene; synthetic polynucleotides; lymphokines such as IFN-γ; IL-2; IL-12; and ISCOMS. See Vogel, *Clin Infect Dis* 30 (suppl 3):S266-270, 2000; Klein et al., 2000, *J Pharm Sci* 89:311-321; Rimmelzwaan et al., 2001, *Vaccine* 19:1180-1187; Kersten, 2003, *Vaccine* 21:915-920; O'Hagen, 2001, *Curr. Drug Target Infect. Disord.* 1:273-286.

Administration

The SEQ ID NO: 2-related polypeptides, immunogens, and pharmaceutical compositions described herein can be formulated and administered to a patient using the guidance provided herein along with techniques well known in the art. Guidelines for pharmaceutical administration in general are provided in, for example, Vaccines Eds. Plotkin and Orenstein, W.B. Sanders Company, 1999; *Remington's Pharmaceutical Sciences* 20$^{th}$ *Edition*, Ed. Gennaro, Mack Publishing, 2000; and *Modern Pharmaceutics* 2$^{nd}$ *Edition*, Eds. Banker and Rhodes, Marcel Dekker, Inc., 1990.

Any suitable route of administration may be employed for providing a patient with the composition of the invention. For example, oral, parenteral, intravenous, intra-articular, intramuscular, intra-dermal, subcutaneous, inhalational, intraperitoneal, transdermal and the like may be employed. Intramuscular and subcutaneous injection is appropriate, for example, for administration of immunogenic compositions, vaccines and DNA vaccines.

The above compositions may be administered in a manner compatible with the dosage formulation, and in such amount as is immunogenically-effective to protect patients from *S. aureus* infection. The dose administered to a patient, in the context of the present invention, should be sufficient to effect a beneficial response in a patient over time such as a reduction in the level of *S. aureus*, or to inhibit infection by *S. aureus*. The quantity of the immunogenic agent(s) to be administered may depend on the subject to be treated inclusive of the age, sex, weight and general health condition thereof. In this regard, precise amounts of the immunogenic agent(s) required to be administered will depend on the judgment of the practitioner. In determining the effective amount of the immunogenic agent to be administered in the treatment or prophylaxis against *S. aureus*, the physician may evaluate circulating plasma levels, progression of disease, and the production of anti-*S. aureus* antibodies. In any event, suitable dosages of the immunogenic agents of the invention may be readily determined by those of skill in the art. Such dosages may be in the order of nanograms to milligrams of the immunogenic agents of the invention.

Suitable dosing regimens are preferably determined taking into account factors well known in the art including age, weight, sex and medical condition of the patient; the route of administration; the desired effect; and the particular compound employed. The immunogen can be used in multi-dose formats. It is expected that a dose would consist of the range of 1.0 μg to 1.0 mg total polypeptide. In different embodiments of the present invention, the dosage range is from 5.0 μg to 500 μg, 0.01 mg to 1.0 mg, or 0.1 mg to 1.0 mg.

The timing of doses depends upon factors well known in the art. After the initial administration one or more additional doses may be administered to maintain and/or boost the appropriate immune response. An example of a dosing regime would be day 1, 1 month, a third dose at either 4, 6 or 12 months, and additional booster doses at distant times as needed.

Patients for Inducing Protective Immunity

A "patient" refers to a mammal capable of being infected with *S. aureus*. In one embodiment, the patient is a human. In alternative embodiments, the patient is a non-human mammal. A patient can be treated prophylactically or therapeutically. Prophylactic treatment provides sufficient protective immunity to reduce the likelihood, or severity, of a *S. aureus* infection. Therapeutic treatment can be performed to reduce the severity of a *S. aureus* infection.

Prophylactic treatment can be performed using a pharmaceutical composition containing a polypeptide or immunogen described herein. Pharmaceutical compositions can be administered to the general population, to infants, children, or the elderly, to immunocompromised patients or to those persons at an increased risk of *S. aureus* infection.

Persons with an increased risk of *S. aureus* infection include health care workers; hospital patients; patients with a weakened immune system; patients undergoing surgery; patients receiving foreign body implants, such as catheter or a vascular device; patients facing therapy leading to a weakened immunity; and, persons in professions having an increased risk of burn or wound injury. See The Staphylococci in Human Disease, Crossley and Archer (ed.), Churchill Livingstone Inc. 1997.

Non-human patients that can be infected with *S. aureus* include cows, pigs, sheep, goats, rabbits, horses, dogs, cats, monkeys, rats and mice. Treatment of non-human patients is useful in protecting pets and livestock, and in evaluating the efficacy of a particular treatment.

Combination Vaccines

An immunogenic agent according to the invention can be mixed, conjugated or fused with other antigens. For example, SA1789 polypeptides can be used alone or in combination with other immunogens to generate a vaccine that is protective against staphylococcal disease or other bacterial diseases; depending on the other immunogens use.

SEQ ID NO: 2-related polypeptides can be used alone, or in combination with other immunogens, to induce an immune response. Additional immunogens that may be present include one or more additional *S. aureus* immunogens, one or more immunogens targeting one or more other *Staphylococcus* organisms such as *S. epidermidis*, *S. pyogenes*, S. haemolyficus, *S. warneri*, or *S. lugunensi* and/or one or more immunogens targeting other infectious organisms including, but not limited to, the pathogenic bacteria *H. influenzae*, *M catarrhalis*, *N. gonorrhoeae*, *E. coli*, *S. pneumoniae*, *C. difficile*, *C. perfringens*, *C. tetani*, bacteria of the genuses *Klebsiella*, *Serratia*, *Enterobacter*, *Proteus*, *Pseudomonas*, *Legionella*, and *Citrobacter*.

A vaccine targeting *S. aureus* can be achieved using suitable *S. aureus* polysaccharides or polypeptides as vaccine components. Examples of polysaccharides that may be employed as possible vaccine components include *S. aureus* type 5 and type 8 capsular polysaccharides. See Shinefield et al., 2002, *N. Eng. J. Med.* 346:491-496. Examples of polypeptides that may be employed as possible vaccine components include clumping factor, collagen adhesin, and fibrinogen binding proteins. See Mamo et al., 1994, *FEMS Immunol. Med. Mic.* 10:47-54; Nilsson et al., 1998, *J. Clin. Invest.* 101:2640-2649; Josefsson et al., 2001, *J. Infect. Dis.* 184: 1572-1580.

The immunogenic agents of the invention may be administered as multivalent subunit vaccines in combination with antigens of other infectious organisms inclusive of the pathogenic bacteria *H. influenzae*, *M. catarrhalis*, *N. gonorrhoeae*, *E. coli*, *S. pneumoniae*, etc.

In one embodiment, the polypeptide of the invention is combined with IsdB (also known as ORF0657n) or related polypeptides. See U.S. Patent Application Publication No. 2006/0177462, incorporated by reference herein in its entirety. Reference to an IsdB immunogen refers to an immunogen that produces a protective immune response that recognizes the IsdB protein in *S. aureus*. An example of an IsdB immunogen is the polypeptide having the sequence of SEQ ID NO: 5. In different embodiments, the IsdB immunogen recognizes at least one or more of the following strains: COL, Becker, MW2, N315, Newman, USA300. The ability of IsdB immunogens to provided protective immunity is illustrated, in for example, U.S. Patent Application Publication No. 2006/0177462, incorporated by reference herein in its entirety.

In additional embodiments, the IsdB immunogen comprises a polypeptide region, said region (a) is at least 90%, at least 94%, at least 95% or at least 99% identical to SEQ ID NO: 5 or a fragment thereof (including, but not limited to, amino acids 42-486, 42-522 and 42-608 of SEQ ID NO: 5); (b) differs from SEQ ID NO: 5 or a fragment thereof (including, but not limited to, amino acids 42-486, 42-522 and 42-608 of SEQ ID NO: 5) by 0, 1, 2, 3, 4, 5, 6, 7, 8, 9, 10, 11, 12, 13, 14, 15, 16, 17, 18, 19, 20, 21, 22, 23, 24, or 25 alterations, or up to 50 alterations; or (c) consists essentially of or consists of SEQ ID NO: 5 or a fragment thereof (including, but not limited to, amino acids 42-486, 42-522 and 42-608 of SEQ ID NO: 5). Examples of alterations include amino acid substitutions, deletions, and insertions.

Examples of one or more additional immunogens include ORF0657n-related polypeptides (Anderson et al., International Publication no. WO 05/009379); ORF0657/ORF0190 hybrid polypeptides (Anderson et al., International Publication no. WO 05/009378); sai-1-related polypeptides (Anderson et al., International Publication no. WO 05/79315); ORF0594-related polypeptides (Anderson et al., International Publication no. WO 05/086663); ORF0826-related polypeptides (Anderson et al., International Publication no. WO 05/115113); PBP4-related polypeptides (Anderson et al., International Publication no. WO 06/033918); AhpC-related polypeptides and AhpC-AhpF compositions (Kelly et al. International Publication No. WO 06/078680); *S. aureus* type 5 and type 8 capsular polysaccharides (Shinefield et al., 2002, *N. Eng. J. Med.* 346:491-496); collagen adhesin, fibrinogen binding proteins, and clumping factor (Mamo et al., 1994, *FEMS Immunol. Med. Microbiol.* 10:47-54; Nilsson et al., 1998, *J. Clin. Invest.* 101:2640-2649; Josefsson et al., 2001, *J. of Infect. Dis.* 184:1572-1580); and polysaccharide intercellular adhesin and fragments thereof (Joyce et al., 2003, *Carbohydrate Research* 338:903-922).

The amount of IsdB can be from 1 to 500 µg, 5 to 200 µg, 10 to 100 µg. Exemplary dosages include, but are not limited to, 10, 20, 30, 40, 50, 60, 70, 80, 90, or 100 µg.

The specific embodiments described herein are offered by way of example only, and the invention is to be limited only by the terms of the appended claims along with the full scope of equivalents to which such claims are entitled. Indeed various modifications of the invention, in addition to those shown and described herein will become apparent to those skilled in the art from the foregoing description and accompanying drawings. Such modifications are intended to fall within the scope of the appended claims.

EXAMPLE 1

Cloning of SA1789

Bacteria isolated from human ascites fluid from clinical samples of tissues infected with *S. aureus* was trypsin digested and the resultant peptide digest subjected to GC-MS analysis and scored using proteomics. Staphylococcal open reading frames (ORF) were prioritized according to the likelihood of surface expression, literature support for in vivo expression, and abundance of expression. Using this process, SA1789 was identified as a potential surface expressed *S. aureus* protein and selected for further study.

Based upon gene sequence information, 2 strategies were employed: 1) to generate the full-length SA1789 (originally designated CHP), and 2) to generate a truncated form lacking the signal peptide at the N-terminus (originally designated ΔCHP).

SA1789 was cloned with a his-tag at the N-terminus with, and without, the 25-aa putative signal peptide. Both constructs were made since the cleavage site for the signal peptide is poor based on sequence analysis.

Constructs +/− the 25 amino acid putative transmembrane domain at the N-terminus (good consensus for signal peptide sequence, but poor signal-peptide cleavage site) were attempted, but expression was obtained with the truncated version only. The recovery of rearranged full-length plasmid DNA and the lack of expression from this construct, suggested that expression of the full-length gene was toxic, even in the absence of induction. Expression of the truncated form was substantially better at 25° C. compared to other temperatures. It was detected entirely in the insoluble fraction, regardless of the temperature of induction or inclusion of a sonication step.

*S. aureus* COL genomic DNA (265 ng) was used as the DNA template w/ Pfu polymerase for PCR amplification of SA1789. Based upon information obtained from the tryptic peptides for SA1789, and the putative signal peptide from amino acids 1-25, a primer at the 5'-end was designed after cleaving off 1-25 aa of 163 aa, i.e. 75 bp.

NdeI was added to the 5'-end of the truncated CHP PCR product and 9 by were left flanking the cloning NdeI site at the 5'-end.

Primers used are shown in Table 2 below. The 2 oligos below are GE-BASE005, 0.05 micromolar scale, and were desalted.

TABLE 2

| Name | Length | Oligo Sequence |
|---|---|---|
| Pr ΔCHP | 42 | GGGAATTCCATATGGTATTAAATTCTGTTAAG AAAAACTTAG (SEQ ID NO: 6) |
| Pr CHP5 (Antisense) | 34 | GGGCTCAGCTTTATCTACTCTAGAAGTATAGC TA (SEQ ID NO: 7) |

The PCR products were digested sequentially with NdeI and BlpI The vector pET16b (Novagen) was treated by dephosphorylation. 15 μg pET16b was digested first with NdeI (60 U) for 2 hr at 37° C. and precipitated with φ-CHCl$_3$-IAA (25:24:1), 7 M NH$_4$Ac, and EtOH. NdeI-digested vector continued to be cut by BlpI (15 U) for 2 hr at 37° C. NdeI-BlpI digested pET 16b was then dephosphorylated for 5' overhang with Calf Intestinal Alkaline Phosphatase (CIAP) for 30 min at 37° C. CIAP-dephosphorylated vector was precipitated with φ-CHCl$_3$-IAA (25:24:1), 7 M NH$_4$Ac, and EtOH again and was resuspended in TE for use. The fragments of NdeI-CHP-BlpI and of NdeI-ΔCHP-BlpI were then cloned into pET16b, respectively and were designated as pCHP5 and pΔCHP5 or ptCHP5 in which the N-terminus was attached to His●Tag. The expression vector (pET) facilitates the addition of either a carboxy or amino his tag to the expressed protein. After blue/white color screening and confirmation of restriction enzyme sites, 3 of 12 clones from pCHP5 appeared to be positive, while 4 of 5 clones from pΔCHP5 were positive.

Capillary DNA Sequencing of pCHP5 and pΔCHP5

Two independent clones from each of pCHP5 and pΔCHP5 were sequenced by Capillary DNA sequencer (Applied Biosystems (ABI) Prism 3100 Genetic Analyzer). The sequences were assembled and edited in Contig Express (Invitrogen Vector NTI). Alignments were performed in AlignX (Invitrogen Vector NTI). It was confirmed that pCHP5 and pΔCHP5 had the correct sequences.

EXAMPLE 2

Expression of Conserved Hypothetical Protein (CHP)

Cells containing pCHP or pΔCHP5 were grown in LB/Amp broth for 6-8 hours at 37° C. and kept overnight at 4° C. When an OD$_{600}$ of the subculture (1:100 dilution of the preculture) reached 0.5-1.0 at 37° C., IPTG was added to induce for 24 hr at 25° C. Sonication was applied to break cells. Cell pellet was treated with BugBuster HT from Novagen to be lysed on ice for 5 minutes. Then the cell suspension was sonicated on ice for 10 seconds for three times. The results showed that at 25° C., ΔCHP5 expressed the highest in terms of the titer and the % total protein. The titer of ΔCHP5 at 25° C. was 90 μg/ml compared to 30 μg/ml at 18° C. and 6 μg/ml at 37° C. The % total protein of ΔCHP5 was 42 compared to 12 at 18° C. and 6 at 37° C. All ΔCHP5 appeared to stay in the insoluble fraction by Coomassie staining (data not shown). ΔCHP5 has a molecular weight of about 18 kDa.

CHP5 was not expressed at any induction temperature. This suggests that either the basal expression of CHP5 was toxic to the cells or DNA rearrangement occurred during PCR cloning.

Recombinant *Staphylococcus aureus* COL ORF SA1789 is an Amp$^R$ transformant of *E. coli* BLR (DE3) and contains plasmid pΔCHP5 encoding the truncated conserved hypothetical protein which has no signal peptide but contains His●Tag at its N-terminus.

EXAMPLE 3

Purification of *E. coli* Expressed Staph Antigens

Frozen cells from *E. coli* expressing SA1789 were thawed and cell paste (109 g) was resuspended in 10 volumes of Buffer A (500 mM NaCl, 5 mM Imidazole, 20 mM Tris, 125 mM Brij-35, 10 mM TritonX-100, 5 mM Tween 20, pH 7.5) containing protease inhibitors. The cells were lysed using a PANDA cell homogenizer (GEA Niro Soavi; Bedford, N.H.). The lysate was clarified at 30,000×g, 60 min, at 4° C. The pellet was resuspended with 20 mM Tris-HCl, 8M Urea, pH 7.5 and subjected to end-over-end mixing for 1 hour at room temperature. The suspension again was clarified at 30,000×g, for 60 minutes, at 4° C. The supernatant was passed over a Ni 6 Sepharose Fast Flow column followed by a washing procedure using 20 mM Tris-HCl pH 7.5 with 8 M Urea. The bound protein was eluted in 10 ml fractions using a linear imidazole gradient of 0-1 M imidazole. Protein containing fractions were analyzed by SDS-PAGE followed by Coomassie—staining or Western blot using anti-His antibody for detection. Fractions containing the SA1789 antigen were pooled and dialyzed into a final buffer containing 2M Urea. From 109 g of cell paste, 0.791 g was isolated. Lysates were prepared by passage through a microfluidizer and the inclusion bodies were isolated by repeated resuspension/centrifugation wash steps. SA1789 was analyzed using SDS-PAGE and Western Blot. From a beginning wet cell weight of 36.7 g, 17.1 g of inclusion bodies was obtained.

Washed inclusion bodies were solubilized in GdHCl, and passed over the IMAC column. The column was washed in renaturation buffer. There was <0.4 mg of protein that eluted in the renaturation elution buffer, and sample was <50% pure. The column was then washed with a GdHCl elution buffer, and ~46 mg of denatured antigen with ~95% purity eluted from the IMAC column.

In order to test different on-column refolding conditions, washed inclusion bodies were solubilized in urea, and passed over the IMAC column. The column was washed in renaturation buffer. No protein eluted in the renaturation elution buffer, and the column was then washed with a Urea elution buffer and ~20 mg of denatured antigen with ~95% purity eluted from the IMAC column A pulse dilution of the GdHCl elution product into a renaturation buffer containing L-Arg was tried followed by stepwise dialysis removal of the denaturant. Following final dialysis ~0.4 mg soluble protein was obtained.

EXAMPLE 4

Rat Indwelling Challenge Model

Purified recombinant protein (SEQ ID NO:3, 20 µg, 0.1 mg/mL) was formulated with Merck amorphous aluminum hydroxyphosphate sulfate adjuvant (AAHSA), and was used to immunize rats in order to generate immune sera. Rats were immunized 3× on days 0, 7 and 21 via the intraperitoneal route. Antisera drawn on day 44 was analyzed for reactivity to the immunogen by ELISA (Table 3). Antigen SACOL1789 was highly immunogenic in rats (Table 3).

TABLE 3

Rat Antisera End Point Titer to SACOL1789

| Test Antigen | End Point ELISA Titer |
|---|---|
| SACOL1789, Day 44 | 325,461 |
| AAHSA, Day 44 | 400 |

Rats immunized with the vaccine underwent surgery to insert an indwelling venous catheter 35 days after the initial administration of the vaccine. Rats were rested for 10 days and then administered a sublethal dose of S. aureus Becker ($2.0 \times 10^9$ CFU/rat) (Strain provided by Chia Lee, University of Arkansas for Medical Sciences, Little Rock); grown in TSA (tryptone soy agar; Becton Dickinson, San Jose, Calif.). The rats were euthanized 24 hours later and the catheters removed using sterile procedures. Catheters were cultured in liquid medium for the presence of S. aureus cells. Detection of S. aureus indicated that the catheter was colonized. The bacteria adherent to each catheter were enumerated using an assay which measured CFU outgrowth versus $OD_{600}$, and comparing to a standard curve of known CFU versus $OD_{600}$.

Results: Two experiments were conducted. In the first experiment, the bacteria load measured on catheters from rats mock vaccinated with adjuvant alone was higher than the CFU measured on catheters from rats vaccinated with SA1789 (GeoMean of 29,099 vs. 2,454 respectively for Rat Study 44), and met the cutoff for significance deemed important for this model (i.e., p=0.3). See FIG. 2. In the second experiment, the number of CFU/catheter was similar for the SA1789 and the mock immunized animals (GeoMean of 318 vs. 271 respectively for Rat Study 53) with p value of 0.45. The combined p value for both experiments was 0.44.

EXAMPLE 5

Murine Lethal Challenge Model

In another approach, female Balb/c mice (6-9 wks) were immunized 3×IM with 20 µg of SdrE or BSA (negative controls), or IsdB (positive control), or SACOL 1789, each formulated on Merck AAHSA, on days 0, 7 and 21. Mice were challenged with a lethal dose ($6.0 \times 10^8$ CFU) of S. aureus Becker (Strain provided by Chia Lee, University of Arkansas for Medical Sciences, Little Rock); grown in TSA (tryptone soy agar; Becton Dickinson, San Jose, Calif.) on day 35 via the tail vein, Survival was monitored over a 10 day period. Sera from days 0 and 28 was titered against the immunizing antigen (Table 4), and antigen SACOL1789 was highly immunogenic in the mice (Table 4).

TABLE 4

Murine End Point ELISA Titers to SACOL1789

| | ELISA end point titers | |
|---|---|---|
| Test Antigen | Exp #1 | Exp #2 |
| SACOL1789, Pre sera titer | 200 | 500 |
| SACOL1789, Post sera titer | 78,026 | 78,294 |

Results: Survival data obtained show a difference between the positive (IsdB) and negative controls (SdrE) indicating that the model was working. Survival was enhanced in mice immunized with SACOL1789 (23/39) versus the negative control antigens SdrE or BSA (12/40), which was significant protection (P<0.01). See Table 5.

TABLE 5

Murine Survival

| | Survival at 10 days post challenge | | |
|---|---|---|---|
| Vaccine Antigen | Exp #1 | Exp #2 | Total |
| SACOL1789 | 13/19 (68%) | 10/20 (50%) | 23/39 (59%) |
| SdrE or BSA Negative control | 8/20 (40%) | 4/20 (20%) | 12/40 (30%) |
| IsdB (0657n) Positive control | 14/20 (70%) | 10/20 (50%) | 24/40 (60%) |
| *P value | 0.055 | 0.0987 | <0.01 |

*log rank (Mantel-Cox), comparing SACOL1789 survival to negative controls SdrE or BSA

What is claimed is:

1. An isolated polypeptide consisting of the amino acid sequence set forth in SEQ ID NO: 2 or the amino acid sequence set forth in SEQ ID NO:2 with an additional N-terminal methionine.

2. The isolated polypeptide of claim 1, wherein said polypeptide is substantially purified.

3. A composition able to induce a protective immune response in a patient against *Staphylococcus aureus* (*S. aureus*) infection comprising an immunologically effective amount of the polypeptide of claim 1 and a pharmaceutically acceptable carrier.

4. The composition of claim 3, wherein the patient is a human or a non-human mammal.

5. The composition of claim 3, wherein said composition further comprises an adjuvant.

6. An isolated polypeptide, that consists of the amino acid sequence set forth in SEQ ID NO: 2 or the amino acid sequence set forth in SEQ ID NO:2 with an additional N-terminal methionine and one or more additional regions or moieties covalently joined to said amino acid sequence, wherein each region or moiety is independently selected from a region or moiety having at least one of the following properties: enhances the immune response, facilitates purification, or facilitates polypeptide stability.

* * * * *

SEQUENCE LISTING

<160> NUMBER OF SEQ ID NOS: 7

<210> SEQ ID NO 1
<211> LENGTH: 489
<212> TYPE: DNA
<213> ORGANISM: Staphylococcus aureus

<400> SEQUENCE: 1

```
atggattgga tttaccaat tgctggaatt atcgctgcga ttgcattctt aattttatgt      60
atcggtatcg tagctgtatt aaattctgtt aagaaaaact tagattatgt tgcaaaaaca    120
cttgacggtg tagaaggtca agttcaaggt attactcgtg aaacaacaga tttacttcat    180
aaagtaaacc gtttaactga ggatatccaa ggtaaagtag atcgtttaaa ctcagttgta    240
gatgctgtta aaggtatcgg tgactcagta caaacgttaa acagctctgt agatcgtgta    300
acaaattcaa ttacacataa tatttctcaa aatgaagata aaatctcaca gttgttcaa     360 tggtcaaatg ttgcaatgga aattgcagac aaatggcaaa atagacacta ccgtcgtgga    420
agtgcaaatt acaaagctaa taatgtagca actgatgcaa atcatagcta tacttctaga    480
gtagataaa                                                            489
```

<210> SEQ ID NO 2
<211> LENGTH: 138
<212> TYPE: PRT
<213> ORGANISM: Staphylococcus aureus

<400> SEQUENCE: 2

Val Leu Asn Ser Val Lys Lys Asn Leu Asp Tyr Val Ala Lys Thr Leu
 1               5                  10                  15

Asp Gly Val Glu Gly Gln Val Gln Gly Ile Thr Arg Glu Thr Thr Asp
                20                  25                  30

Leu Leu His Lys Val Asn Arg Leu Thr Glu Asp Ile Gln Gly Lys Val
            35                  40                  45

Asp Arg Leu Asn Ser Val Val Asp Ala Val Lys Gly Ile Gly Asp Ser
        50                  55                  60

Val Gln Thr Leu Asn Ser Ser Val Asp Arg Val Thr Asn Ser Ile Thr
65                  70                  75                  80

His Asn Ile Ser Gln Asn Glu Asp Lys Ile Ser Gln Val Val Gln Trp
                85                  90                  95

Ser Asn Val Ala Met Glu Ile Ala Asp Lys Trp Gln Asn Arg His Tyr
                100                 105                 110

Arg Arg Gly Ser Ala Asn Tyr Lys Ala Asn Asn Val Ala Thr Asp Ala
            115                 120                 125

Asn His Ser Tyr Thr Ser Arg Val Asp Lys
        130                 135

<210> SEQ ID NO 3
<211> LENGTH: 163
<212> TYPE: PRT
<213> ORGANISM: Artificial Sequence
<220> FEATURE:
<223> OTHER INFORMATION: SA1789 protein with amino terminal His-tag and
      three additional amino acids at carboxy terminus

<400> SEQUENCE: 3

Met Gly His His His His His His His His His Ser Ser Gly His
 1               5                  10                  15

Ile Glu Gly Arg His Met Val Leu Asn Ser Val Lys Lys Asn Leu Asp

```
                20                  25                  30
Tyr Val Ala Lys Thr Leu Asp Gly Val Glu Gly Gln Val Gln Gly Ile
        35                  40                  45

Thr Arg Glu Thr Thr Asp Leu Leu His Lys Val Asn Arg Leu Thr Glu
    50                  55                  60

Asp Ile Gln Gly Lys Val Asp Arg Leu Asn Ser Val Val Asp Ala Val
65                  70                  75                  80

Lys Gly Ile Gly Asp Ser Val Gln Thr Leu Asn Ser Ser Val Asp Arg
                85                  90                  95

Val Thr Asn Ser Ile Thr His Asn Ile Ser Gln Asn Glu Asp Lys Ile
            100                 105                 110

Ser Gln Val Val Gln Trp Ser Asn Val Ala Met Glu Ile Ala Asp Lys
        115                 120                 125

Trp Gln Asn Arg His Tyr Arg Arg Gly Ser Ala Asn Tyr Lys Ala Asn
    130                 135                 140

Asn Val Ala Thr Asp Ala Asn His Ser Tyr Thr Ser Arg Val Asp Lys
145                 150                 155                 160

Ala Glu Gln

<210> SEQ ID NO 4
<211> LENGTH: 163
<212> TYPE: PRT
<213> ORGANISM: Staphylococcus aureus
<220> FEATURE:

<400> SEQUENCE: 4

Met Asp Trp Ile Leu Pro Ile Ala Gly Ile Ile Ala Ala Ile Ala Phe
1               5                   10                  15

Leu Ile Leu Cys Ile Gly Ile Val Ala Val Leu Asn Ser Val Lys Lys
            20                  25                  30

Asn Leu Asp Tyr Val Ala Lys Thr Leu Asp Gly Val Glu Gly Gln Val
        35                  40                  45

Gln Gly Ile Thr Arg Glu Thr Thr Asp Leu Leu His Lys Val Asn Arg
    50                  55                  60

Leu Thr Glu Asp Ile Gln Gly Lys Val Asp Arg Leu Asn Ser Val Val
65                  70                  75                  80

Asp Ala Val Lys Gly Ile Gly Asp Ser Val Gln Thr Leu Asn Ser Ser
                85                  90                  95

Val Asp Arg Val Thr Asn Ser Ile Thr His Asn Ile Ser Gln Asn Glu
            100                 105                 110

Asp Lys Ile Ser Gln Val Val Gln Trp Ser Asn Val Ala Met Glu Ile
        115                 120                 125

Ala Asp Lys Trp Gln Asn Arg His Tyr Arg Arg Gly Ser Ala Asn Tyr
    130                 135                 140

Lys Ala Asn Asn Val Ala Thr Asp Ala Asn His Ser Tyr Thr Ser Arg
145                 150                 155                 160

Val Asp Lys

<210> SEQ ID NO 5
<211> LENGTH: 645
<212> TYPE: PRT
<213> ORGANISM: Staphylococcus aureus

<400> SEQUENCE: 5

Met Asn Lys Gln Gln Lys Glu Phe Lys Ser Phe Tyr Ser Ile Arg Lys
1               5                   10                  15
```

-continued

```
Ser Ser Leu Gly Val Ala Ser Val Ala Ile Ser Thr Leu Leu Leu Leu
         20                  25                  30

Met Ser Asn Gly Glu Ala Gln Ala Ala Glu Glu Thr Gly Gly Thr
         35                  40                  45

Asn Thr Glu Ala Gln Pro Lys Thr Glu Ala Val Ala Ser Pro Thr Thr
 50                  55                  60

Thr Ser Glu Lys Ala Pro Glu Thr Lys Pro Val Ala Asn Ala Val Ser
 65                  70                  75                  80

Val Ser Asn Lys Glu Val Glu Ala Pro Thr Ser Glu Thr Lys Glu Ala
                     85                  90                  95

Lys Glu Val Lys Glu Val Lys Ala Pro Lys Glu Thr Lys Glu Val Lys
                 100                 105                 110

Pro Ala Ala Lys Ala Thr Asn Asn Thr Tyr Pro Ile Leu Asn Gln Glu
             115                 120                 125

Leu Arg Glu Ala Ile Lys Asn Pro Ala Ile Lys Asp Lys Asp His Ser
         130                 135                 140

Ala Pro Asn Ser Arg Pro Ile Asp Phe Glu Met Lys Lys Lys Asp Gly
145                 150                 155                 160

Thr Gln Gln Phe Tyr His Tyr Ala Ser Ser Val Lys Pro Ala Arg Val
                 165                 170                 175

Ile Phe Thr Asp Ser Lys Pro Glu Ile Glu Leu Gly Leu Gln Ser Gly
             180                 185                 190

Gln Phe Trp Arg Lys Phe Glu Val Tyr Glu Gly Asp Lys Lys Leu Pro
         195                 200                 205

Ile Lys Leu Val Ser Tyr Asp Thr Val Lys Asp Tyr Ala Tyr Ile Arg
     210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                 245                 250                 255

Ala Gln Pro Ile Tyr Asn Ser Ala Asp Lys Phe Lys Thr Glu Glu Asp
             260                 265                 270

Tyr Lys Ala Glu Lys Leu Leu Ala Pro Tyr Lys Lys Ala Lys Thr Leu
         275                 280                 285

Glu Arg Gln Val Tyr Glu Leu Asn Lys Ile Gln Asp Lys Leu Pro Glu
290                 295                 300

Lys Leu Lys Ala Glu Tyr Lys Lys Leu Glu Asp Thr Lys Lys Ala
305                 310                 315                 320

Leu Asp Glu Gln Val Lys Ser Ala Ile Thr Glu Phe Gln Asn Val Gln
                 325                 330                 335

Pro Thr Asn Glu Lys Met Thr Asp Leu Gln Asp Thr Lys Tyr Val Val
             340                 345                 350

Tyr Glu Ser Val Glu Asn Asn Glu Ser Met Met Asp Thr Phe Val Lys
         355                 360                 365

His Pro Ile Lys Thr Gly Met Leu Asn Gly Lys Lys Tyr Met Val Met
     370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                 405                 410                 415

Ile Phe Pro Tyr Val Glu Gly Lys Thr Leu Tyr Asp Ala Ile Val Lys
             420                 425                 430

Val His Val Lys Thr Ile Asp Tyr Asp Gly Gln Tyr His Val Arg Ile
         435                 440                 445
```

Val Asp Lys Glu Ala Phe Thr Lys Ala Asn Thr Asp Lys Ser Asn Lys
            450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
            515                 520                 525

Pro Thr Lys Gly Glu Val Glu Ser Ser Thr Thr Pro Thr Lys Val
            530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
            595                 600                 605

Ser Leu Pro Gln Thr Gly Glu Glu Ser Asn Lys Asp Met Thr Leu Pro
610                 615                 620

Leu Met Ala Leu Leu Ala Leu Ser Ser Ile Val Ala Phe Val Leu Pro
625                 630                 635                 640

Arg Lys Arg Lys Asn
            645

<210> SEQ ID NO 6
<211> LENGTH: 42
<212> TYPE: DNA
<213> ORGANISM: Artificial Sequence
<220> FEATURE:
<223> OTHER INFORMATION: SA1789 PCR primer, forward

<400> SEQUENCE: 6
gggaattcca tatggtatta aattctgtta agaaaaactt ag         42

<210> SEQ ID NO 7
<211> LENGTH: 34
<212> TYPE: DNA
<213> ORGANISM: Artificial Sequence
<220> FEATURE:
<223> OTHER INFORMATION: SA1789 PCR primer, reverse

<400> SEQUENCE: 7
gggctcagct ttatctactc tagaagtata gcta         34